United States Patent [19]

Adrian

[11] 4,156,143

[45] May 22, 1979

[54] DEVICE FOR MEASURING THE CONCENTRATION OF A GAS

[76] Inventor: Werner Adrian, Im Roth 19, D-7505 Ettlingen-Oberweier, Fed. Rep. of Germany

[21] Appl. No.: 868,371

[22] Filed: Jan. 10, 1978

[51] Int. Cl.² ............................................. G01N 21/26
[52] U.S. Cl. .................................................. 250/343
[58] Field of Search ............... 250/343, 344, 345, 373; 356/51, 201, 204

[56] References Cited

U.S. PATENT DOCUMENTS 4,057,724  11/1977  Adrian et al. ........................ 250/343

*Primary Examiner*—Davis L. Willis
*Attorney, Agent, or Firm*—Colton & Stone, Inc.

[57] ABSTRACT

A device as described whereby the concentration of a gas such as alcohol vapor can be measured using radiation absorption techniques in a chamber. The chamber is an elongated tube having a window at one end through which infra red radiation can pass with an optical reflector at the two ends of the tube and at least one other reflector for causing the reflected radiation to leave the tube through a second window in the side of the tube, from where it passes to a detector.

Sensitivity is increased by passing the radiation in series through a number of parallel arranged chambers which conveniently are located within a common housing.

12 Claims, 3 Drawing Figures

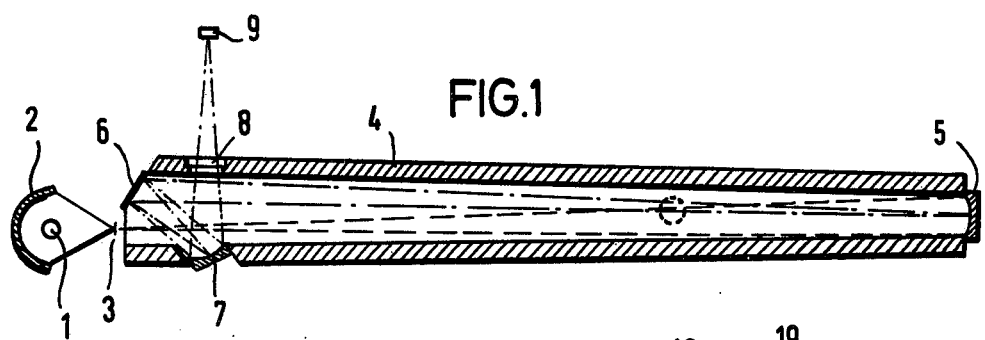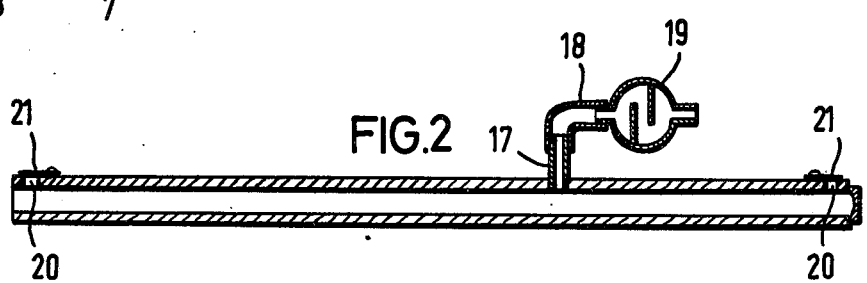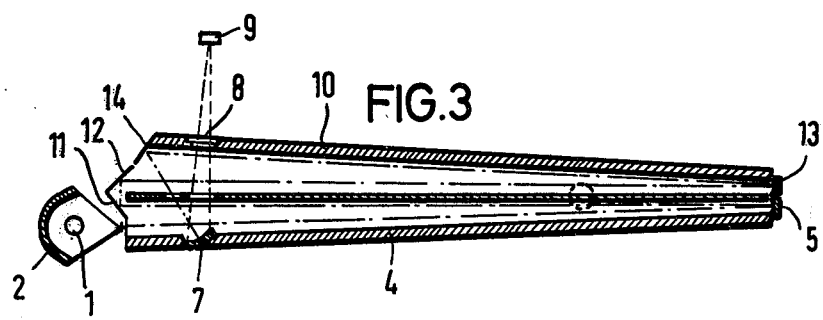

DEVICE FOR MEASURING THE CONCENTRATION OF A GAS

FIELD OF INVENTION

This invention relates to a device for measuring the concentration of a gas particularly alcohol vapour. In this specification the term "gas" will be used to mean any gaseous or vaporised substance.

BACKGROUND TO INVENTION

In the known devices for measuring the concentration of gases by radiation absorption at characteristic absorption wave lengths for the gas, the gas to be analysed is introduced into a measuring chamber. This is subjected to radiation of the specific wave length which enters the measuring chamber with a flux $\phi_o$. This flux is weakened if gas molecules having a significant absorption characteristic at that wave-length are present and if present, the radiation leaves the measuring chamber with a reduced flux $\phi$.

According to Lambert-Beer's law, the relationship is written:

$$\phi = \phi_o e^{-mlc}$$

where
- m is a material constant,
- l is the length of the radiation path in the absorbing medium, and
- c is the concentration of the absorbing gas in the measuring chamber.

If it is desired to measure very small concentrations, then, for a minimum weakening ratio which is given by the relationship $\phi/\phi_o$ and is limited by the resolution and sensitivity of the detectors and amplifiers, this is only possible by increasing the path length l of the radiation through the chamber.

In known spectrophotometric devices for gas analysis, measuring chambers are used in which the radiation path is bent via an optical system. For example, a principle given by White makes it possible to produce path lengths of up to ten meters. However, the apertures are small and the volume of the chamber amounts to more than six liters. For measuring the concentration of alcohol molecules in exhaled breath, the measuring chamber must have a very small volume in order to ensure that only air from deep in the lungs fills the measuring chamber. For this reason the chamber volume must not exceed 100 $cm^3$.

A device is described in U.S. Pat. No. 3,319,071 in which a sphere with highly reflective inner walls forms the measuring chamber. However, this arrangement is quite unsuitable for measuring the concentration of alcohol in the breath, as a sphere has the greatest volume with the smallest outer dimensions and exactly the opposite is desired.

OBJECTS OF THE INVENTION

On this basis, it is the object of the invention to produce a device with a measuring chamber having an extremely small volume, a long radiation path and a high efficacy.

THE INVENTION

According to the present invention a device for measuring the concentration of gases by radiation absorption comprises a chamber in the form of an elongate tube, inlet and outlet means in the chamber for the inflow and outflow of gases to be analysed, a first window in one end of the chamber through which infra red (IR) radiation can enter the chamber, a source of IR radiation, an ellipsoidal concave reflector for reflecting IR radiation positioned so that the radiation source is situated at one of the two focal points thereof and so that IR radiation reflected by the ellipsoidal reflector enters the chamber through the said first window, the second focal point of the ellipsoidal reflector lying on the path of the reflected radiation, first optically reflecting means at the opposite end of the chamber for reflecting IR radiation which traverses the chamber along a first path back towards the said one end of the chamber along a second different path, second optically reflecting means located on said second path for reflecting IR radiation along at least a third path different from the first and second paths, thereby to leave the chamber, and a radiation detector for receiving and responding to radiation leaving the chamber.

Where the measuring chamber is to be fitted to a device for measuring the concentration of alcohol in exhaled breath, the gas inlet means preferably comprises a side tube communicating with an aperture in the wall of the chamber and a saliva trap is connected between the said side tube and nozzle into which a subject under test can exhale.

Preferably the source of radiation comprises an ellipsoidal quartz-halogen lamp of the type which is vacuum-coated with gold. The rays are concentrated at the second focal point of the ellipsoid. Due to the length of the coil and irregularities usually present in the surface of the ellipsoidal mirror, a point of focus of approximately 6 mm diameter is obtained from such lamps. For the purpose of this invention this is sufficiently punctiform and the point of focus is formed on the said first window in the chamber.

With optically reflecting elements arranged at opposite ends of the measuring chamber, radiation entering the chamber is reversed in direction at each end and in a basic embodiment of the invention it can be made to pass through the measuring chamber at least twice. Ideally the image of the radiation source created at the second focal point of the ellipsoidal concave reflector or lamp will be projected back in approximately the same plane by the first optically reflecting means located at the opposite end of the chamber. This image will appear on the second optically reflecting means which in turn reflects the reduced image from the illuminating surface of the first optically reflecting means onto the detector.

Preferably the interior of the chamber is highly reflective of IR radiation so that any IR radiation falling thereon is reflected and finally impinges on one of the reflecting means so that this radiation also reaches the detector, possibly after many reflections but nevertheless increasing the overall efficiency of the device. The radiation losses in a measuring chamber constructed in accordance with this preferred feature of the invention can therefore be small.

In order to keep the losses within the chamber as small as possible the focal length of the first optically reflecting means is preferably equal to half the length of the measuring chamber and that of the second optically reflecting means is equal to the distance between it and the detector, which typically is short in comparison with the length of the measuring chamber.

It is better if the detector is arranged in such a way that it does not receive any direct irradiation from the source. Consequently the second optically reflecting means is preferably offset laterally from the radiation inlet on or in the wall of the measuring chamber and a plane reflector is arranged in the measuring chamber next to the radiation inlet. In this way the reduced image of the radiation source which falls on the detector is created at a point which can be shielded from the effect of the heat from the radiation source and is removed from the radiation inlet.

In order to keep the volume of the measuring chamber as small as possible, the measuring chamber is made wider at the end containing the first window than at its further end, and its cross-section reduces between these two ends along one plane. This design makes it possible to accommodate a plane reflector next to the radiation inlet without reducing the size of the aperture of the optically reflecting means within the chamber.

In an embodiment of the invention comprising a single chamber, the second optically reflecting means may comprise a plane reflector for reflecting the radiation from the said second path along an intermediate path and a convex reflector on said intermediate path for reflecting the radiation from the said intermediate path along a third path out of the chamber. To this end a second window is located in the side wall of the tube and the detector is located laterally of the tube beyond the second window and the focal length of the convex reflector is chosen to be short compared with the length of the tube.

Each of the optically reflecting means may comprise a concave reflector or a plane reflecting element having a convex lens mounted in front thereof.

In a development of the invention the tubular chamber is duplicated and the IR radiation transfers from one chamber to the next and after traversing each chamber in turn finally leaves the last chamber for the detector. In this development of the invention the length of the overall path is increased considerably. In an embodiment of this development, two or more measuring chambers are arranged adjacent to each other, the measuring chambers having at one end optically reflecting elements and at the other end plane reflectors directed towards the optically reflecting elements and towards each other, the last of the reflecting means in the radiation path being directed towards the detector. In such an embodiment two or more measuring chambers can thus be considered to be adjacent to each other each having the same length and representing an increase in the overall width of the device but a significant multiplication of the path length for the radiation between inlet and outlet is obtained and sensitivity can be increased.

In an embodiment such as just described, it has been found expedient to arrange a further plane reflector between the last plane reflector and the detector and a focusing lens mounted in front.

By incorporating the invention, a small chamber volume can be combined with a long effective path length for the infra red radiation through the chamber and a high degree of efficiency can be obtained since the flux of radiation beamed into the chamber through the inlet window is only weakened by the small losses of the reflectors and of the highly polished reflecting inner walls.

The invention will now be described by way of example with reference to the accompanying drawings.

IN THE DRAWINGS

FIG. 1 is a cross-section through an embodiment in which the measuring chamber widens out in one plane, from one end to the other, FIG. 2 is a cross-section through this embodiment at right angles to the first showing the parallel walls, and shows the inlet and outlets for the gas to be analysed, and FIG. 3 is a cross-section through another embodiment in which two measuring chambers are arranged adjacent to each other in a common housing.

DETAILED DESCRIPTION OF EMBODIMENTS

FIG. 1 shows a radiation source 1 arranged at a focal point of an ellipsoidal reflector 2. The radiation flux emitted by this is focused at the second focal point 3. The radiation inlet to the measuring chamber 4 is located here. An optically reflecting element 5 arranged at the far end of the measuring chamber projects the second focal point of the ellipsoidal reflector 2 via a plane reflector 6 to a laterally located second optically reflecting element 7. The radiating surface of the first optically reflecting element is projected by the second optically reflecting element via an opening 8 onto a detector 9. Thus, the radiation coming from the radiation source 1 passes through the measuring chamber 4 rather more than twice before it reaches the detector 9.

The arrangement of the two optically reflecting elements 5 and 7 at the opposite ends of the measuring chamber is decisive for the optical principle of the invention here. The interposition of the plane reflector 6 is of no importance to the invention. The plane reflector 6 serves only to project the radiation via the second optically reflecting element 7 out of the measuring chamber 4 onto the detector 9. This can then be arranged to advantage some distance from the radiation source 1.

FIG. 2 shows the tube 4 which forms the measuring chamber with a gas inlet connection 17 which is connected via a piece of tubing 18 to a saliva trap 19. The gas inlet connection 17 is arranged towards the narrower end of the tube. In the vicinity of each of the ends there is an air outlet hole 20. These are covered by sprung plates 21 which form flap valves. These are approximately 0.05 mm thick and are each held by a screw with a pressure disc. They act as overflow valves. When breath is blown in via the saliva trap 19 the inner pressure lifts the sprung plates 21. Excess gas can thus escape from the measuring chamber 4.

FIG. 3 shows a double measuring chamber in which the described principle is applied twice. The radiation coming from the radiation source 1 reaches the optically reflecting element 5 in the way described, and from there arrives at a first plane reflector 11, which conducts the radiation via a second plane reflector 12 arranged at 90° to its plane, into the second chamber. The dividing wall between the two chambers is necessary so that the radiation which arises due to reflections from the interior wall surfaces can be evaluated at the same time. In the second measuring chamber the principle already described in relation to the single measuring chamber is repeated. The image of the second focal plane is reflected from the optically reflecting element 13 after deflection via the plane reflector onto the laterally arranged optically reflecting element 7, which again focuses the radiation on the detector 9. In this embodiment, the essential point is that the radiation traverses each measuring chamber twice, so that a considerable increase in path length is obtained and the radiation flux is finally focused at a point removed from the radiation source, without the need to proportionally increase the volume of the overall device to accommodate the additional path length.

Modifications are possible within the scope of the invention. Thus, the optically reflecting elements can be constructed either as concave reflectors or as plane reflectors with offset focusing lenses. Similarly, the spatial positions of the radiation source and the detector can be transposed.

As a modification to the construction form shown in FIG. 1, the plane reflector 6 can also be arranged rotated in a counter-clockwise direction. The radiation then arrives on the detector 9 after being concentrated through a focusing lens, without interposing the optically reflecting element 7. The same applies for the construction form according to FIG. 3. Here, the plane reflector 14 and the focusing lens deflect the radiation directly onto the detector 9.

Within the scope of the invention, the embodiment shown in FIG. 3 can also be modified so that the optically reflecting element 13 is omitted and the second measuring chamber 10 has a radiation outlet in its place. A focusing lens may then be arranged behind this outlet to project the radiation onto the detector. In this event the second measuring chamber is only traversed in one direction.

Similarly, the optically reflecting element 13 can be rotated so that it projects the radiation directly onto a detector. However, for this it must comprise a concave reflector with a short focal length.

I claim:

1. A device for measuring the concentration of gases by radiation absorption comprising:
   a chamber in the form of an elongate tube the interior surface of which is highly reflective to infra red radiation;
   inlet and outlet means in the chamber for the inflow and outflow of gases to be analysed;
   a first window in one end of the chamber through which infra red radiation can enter the chamber;
   a source of infra red radiation;
   an ellipsoidal concave reflector for reflecting infra red radiation positioned so that the radiation source is situated at one of the two focal points thereof and so that infra red radiation reflected by the ellipsoidal reflector enters the chamber through the said first window, the second focal point of the ellipsoidal reflector lying on the path of the reflected radiation;
   first optically reflecting means at the opposite end of the chamber for reflecting infra red radiation which transverses the chamber along a first path back towards the said one end of the chamber along a second different path;
   second optically reflecting means located on said second path for reflecting infra red radiation along at least a third path;
   a radiation detector for receiving and responding to radiation leaving the chamber;
   and further characterized in that there are at least two tubular chambers and the infra red radiation is transferred from one chamber to the next and, after traversing each chamber in turn, leaves the last chamber to pass to the detector.

2. A device as set forth in claim 1 wherein the first window is located at the second focal point of the ellipsoidal reflector.

3. A device as set forth in claim 1 wherein the focal length of the first optically reflecting means located at the end of the chamber remote from the first window is equal to half the length of the measuring chamber.

4. A device as set forth in claim 1 wherein the second optically reflecting means comprises a plane reflector for reflecting the radiation from the said second path along an intermediate path and a convex reflector on said intermediate path for reflecting the radiation from the said intermediate path along the said third path and from thence out of the chamber.

5. A device as set forth in claim 4 wherein a second window is located in the side wall of the tube and the detector is located laterally of the tube beyond the said second window.

6. A device as set forth in claim 5 wherein the focal length of the convex reflector is short compared with the length of the tube.

7. A device as set forth in claim 1 wherein the width of the measuring chamber decreases in the direction from the end containing the said first window to the end containing the said first optically reflecting means.

8. A device as set forth in claim 1 in which each optically reflecting means comprises a concave reflector.

9. A device as set forth in claim 1 wherein each optically reflecting means comprises a plane reflecting element and a convex lens located in front thereof.

10. A device as set forth in claim 1 for measuring the concentration of alcohol in exhaled breath, in which the gas inlet to the chamber comprises
    a side tube communicating with an aperture in the wall of the chamber,
    a saliva trap located in said side tube, and
    a nozzle at the entrance to the saliva trap into which exhaled breath can pass.

11. A device as set forth in claim 1 wherein the radiation source comprises a quartz-halogen lamp.

12. A device as set forth in claim 11 wherein the lamp is an ellipsoidal quartz-halogen lamp which is vacuum-coated with gold.

* * * * *